(12) United States Patent
Ohashi et al.

(10) Patent No.: US 6,475,248 B2
(45) Date of Patent: Nov. 5, 2002

(54) HAIR DYE COMPOSITION

(75) Inventors: Yukihiro Ohashi; Hajime Miyabe; Kenichi Matsunaga; Shintaro Totoki; Yoshinori Saito, all of Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/886,982

(22) Filed: Jun. 25, 2001

(65) Prior Publication Data

US 2002/0026676 A1 Mar. 7, 2002

(30) Foreign Application Priority Data

Jun. 27, 2000 (JP) .................................. 2000-193176

(51) Int. Cl.$^7$ ................................................. A61K 7/13
(52) U.S. Cl. ........................ 8/405; 8/405; 8/406; 8/426; 8/437
(58) Field of Search ........................... 8/405, 406, 426, 8/437

(56) References Cited

U.S. PATENT DOCUMENTS

| | | | | |
|---|---|---|---|---|
| 2,872,449 A | * | 2/1959 | Hans et al. ................ 260/157 |
| 2,922,690 A | * | 1/1960 | Roland et al. ................. 8/21 |
| 3,529,927 A | | 9/1970 | Ulrich ......................... 8/171 |
| 3,545,914 A | | 12/1970 | Hayashi et al. .............. 8/169 |
| 4,017,255 A | | 4/1977 | Cobb ........................... 8/21 B |
| 4,168,144 A | * | 9/1979 | Kenneth et al. .............. 8/10.1 |
| 5,174,790 A | | 12/1992 | Riggins et al. ............... 8/490 |
| 5,258,065 A | | 11/1993 | Fujisawa .................... 106/22 B |
| 6,004,355 A | * | 12/1999 | Dias et al. .................... 8/406 |

* cited by examiner

*Primary Examiner*—Yogendra N. Gupta
*Assistant Examiner*—Eisa Elhilo
(74) *Attorney, Agent, or Firm*—Oblon, Spivak, McClelland, Maier & Neustadt, P.C.

(57) ABSTRACT

Provided is a hair dye composition containing a direct dye (1). This hair dye composition has markedly high hair dyeing power, has less color fade over time and undergoes a small change in the color tone of the dye even after storage.

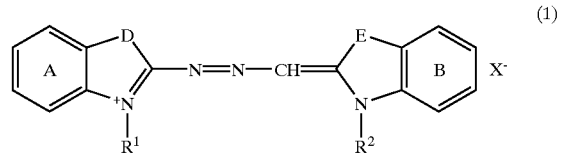

wherein, rings A and B represents a benzene ring which may have a substituent and may further be cyclocondensed with another aromatic ring, D and E each independently represents a group $NR^3$ (in which $R^3$ represents a $C_{1-6}$ alkyl group) or an S atom, $R^1$ and $R^2$ each independently represents a $C_{1-6}$ alkyl group, and $X^-$ represents an anion.

19 Claims, No Drawings

HAIR DYE COMPOSITION

TECHNICAL FIELD

The present invention relates to a hair dye composition having markedly high dyeing power, can strongly impart the hair with an extremely vivid color ranging from greenish yellow to yellow, has less color fade over time and undergoes a small change in the color tone of the dye even after storage.

BACKGROUND ART

Hair dyes can be classified by the dye to be used therefor, or whether they have bleaching action of melanin or not. Typical examples include a two-part permanent hair dye composed of a first part containing an alkali agent, an oxidation dye and a direct dye such as nitro dye and a second part containing an oxidizing agent; and one-part semi-permanent hair dye containing an organic acid or an alkali agent, and a direct dye such as acid dye, basic dye or nitro dye.

The above-described permanent hair dye is however accompanied with the drawbacks that color tone imparted by an oxidation dye is not so vivid and the color of the hair dyed with a vivid-color producing nitro dye ordinarily employed as a direct dye markedly fades over time and becomes dull soon even if the color tone rightly after dyeing is very vivid (Japanese Patent Application Laid-Open (Kokai) No. Hei 6-271435).

Recently, hair dyes containing as a direct dye a so-called cationic dye having a cation group contained in their conjugate system have been reported (Japanese Language Laid-Open Publication (PCT) No. Hei 8-507545, 8-501322 or 10-502946, or Japanese Patent Application Laid-Open (Kokai) No. Hei 10-194942). They have been found to involve drawbacks that intended dyeing effects are not available owing to decomposition of them caused by mixing, upon hair dyeing, with hydrogen peroxide ordinarily employed as an oxidizing agent; and that they are unstable to an alkali agent or a reducing agent essentially contained in a permanent hair dye.

DISCLOSURE OF THE INVENTION

An object of the present invention is to provide a hair dye composition which has high hair dyeing power, less color fade over time, and excellent storage stability to permit only a small change in color tone of the dye after storage.

The present inventors have found that when the below-described compound which is known as a cationic dye for dyeing or printing therewith fiber materials, paper or leather and is typified by Basic Yellow 24 is used as a hair dye, the resulting dye composition can strongly impart the hair with a vivid color ranging from greenish yellow to yellow without decomposing the dye upon hair dyeing, exhibits excellent light resistance, washing resistance, perspiration resistance, friction resistance and heat resistance, and undergoes a small change in the color tone of the dye after storage as compared with that rightly after preparation because the dye exists in the composition stably.

In one aspect of the present invention, there is thus provided a hair dye composition comprising, as a direct dye, a compound represented by the following formula (1):

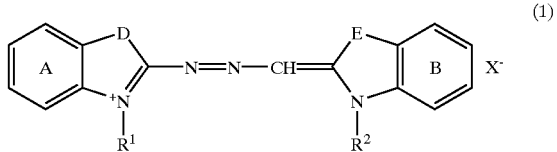

wherein, rings A and B each independently represents a benzene ring which may have a substituent and may further be cyclocondensed with another aromatic ring;

D and E each independently represents a group $NR^3$ (in which $R^3$ represents a $C_{1-6}$ alkyl group) or a sulfur atom, $R^1$ and $R^2$ each independently represents a $C_{1-6}$ alkyl group, and $X^-$ represents an anion.

In another aspect of the present invention, there is also provided a method for dyeing the hair with the above-described hair dye composition.

BEST MODE FOR CARRYING OUT THE INVENTION

In the formula (1), examples of the substituent which the ring A or B may have include alkyl groups, aryl groups, alkoxy groups, amino group, hydroxy group, cyano group, nitro group and hydrogen atoms, more specifically, methyl group, ethyl group, methoxy group, ethoxy group, chlorine atom and bromine atom.

Examples of the $C_{1-6}$ alkyl group represented by $R^1$, $R^2$ or $R^3$ include methyl, ethyl, propyl, isopropyl and cyclohexyl groups.

Examples of the anion represented by $X^-$ in the formula (1) include chloride ions, bromide ions, iodide ions, trichlorozincic acid ions, tetrachlorozincic acid ions, sulfuric acid ions, hydrosulfuric acid ions, methyl sulfate ions, phosphoric acid ions, formic acid ions and acetic acid ions.

The following Basic Yellow 24 can be given as a specific example of the direct dyes (1) to be used in the present invention.

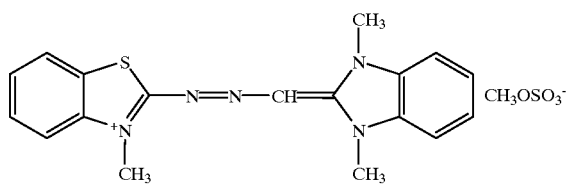

As a direct dye, at least one of the direct dyes (1) can be used, or another direct dye can be used in combination. In particular, combination with red and blue dyes makes it possible to dye the hair with a deep and highly lustrous dark brown or black color.

Examples of the direct dye other than the direct dyes (1) include Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 22 (C.I. 11055), Basic Red 76 (C.I. 12245), Basic Red 118 (C.I. 12251:1) and Basic Yellow 57 (C.I. 12719); and basic dyes as described in Japanese Patent Publication No. Sho 58-2204, Japanese Patent Application Laid-Open No. Hei 9-118832, Japanese Language Laid- Open Publication (PCT) No. Hei 8-501322 or Japanese Language Laid-Open Publication (PCT) No. Hei 8-507545.

The direct dye (1) is preferably added in an amount of 0.01 to 20 wt. %, more preferably 0.05 to 10 wt. %, especially 0.1 to 5 wt. % based on the whole composition (after mixture of all the component parts when the hair dye composition is a two part or three part type; this will apply equally hereinafter). When another direct dye is used in combination, the content of it in total with the direct dye (1) preferably ranges from 0.05 to 10 wt. %, especially 0.1 to 5 wt. %.

The hair dye composition of the present invention is preferably adjusted to pH 6 to 11, with pH 8 to 11 being especially preferred. Examples of the alkali agent to be used for pH adjustment include ordinarily employed ones such as ammonia, organic amines and salts thereof. The alkali agent is preferably added in an amount of 0.01 to 20 wt. %, more preferably 0.1 to 10 wt. %, especially 0.5 to 5 wt. % based on the whole composition.

In the hair dye composition of the present invention, an oxidizing agent can be incorporated. In this case, hair dyeing and bleaching can be carried out simultaneously, which facilitates more vivid hair dyeing. Ordinarily employed oxidizing agents, for example, hydrogen peroxide, persulfates such as ammonium persulfate, potassium persulfate and sodium persulfate, perborates such as sodium perborate, percarbonates such as sodium percarbonate and bromates such as sodium bromate and potassium bromate are usable. Out of them, hydrogen peroxide is especially preferred. The oxidizing agent is preferably added in an amount of 0.5 to 10 wt. %, especially 1 to 8 wt. %, based on the whole composition.

In the hair dye composition of the present invention, an oxidation dye can be incorporated further. This incorporation enables markedly vivid dyeing not attainable by the single use of an oxidation dye. In this case, the above-exemplified oxidizing agents can be used as an oxidizing agent, with hydrogen peroxide being particularly preferred. Alternatively, an oxidizing enzyme such as laccase can be employed. For the oxidation dye, known color developers and couplers ordinarily employed for an oxidation type hair dye can be used.

Examples of the developer include p-phenylenediamines having one or several groups selected from $NH_2$—, NHR— and $NR_2$— groups (wherein, R represents a $C_{1-4}$ alkyl or hydroxyalkyl group) such as p-phenylenediamine, p-toluylenediamine, N-methyl-p-phenylenediamine, chloro-p-phenylenediamine, 2-(2'-hydroxyethylamino)-5-aminotoluene, N,N-bis-(2-hydroxyethyl)-p-phenylenediamine, 2-hydroxyethyl-p-phenylenediamine, 2,6-dimethyl-p-phenylenediamine, methoxy-p-phenylenediamine, 2,6-dichloro-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine and N-2-methoxyethyl-p-phenylenediamine; 2,5-diaminopyridine derivatives and 4,5-diaminopyrazole derivatives, p-aminophenols such as p-aminophenol, 2-methyl-4-aminophenol, N-methyl-p-aminophenol, 3-methyl-4-aminophenol, 2,6-dimethyl-4-aminophenol, 3,5-dimethyl-4-aminophenol, 2,3-dimethyl-4-aminophenol and 2,5-dimethyl-4-aminophenol; o-aminophenols, o-phenylenediamines, 4,4'-diaminophenylamine and hydroxypropylbis(N-hydroxyethyl-p-phenylenediamine); and salts thereof.

Examples of the coupler include 1-naphthol, 1,5-dihydroxynaphthalene, 1,7-dihydroxynaphthalene, 2,7-dihydroxynaphthalene, 5-amino-2-methylphenol, 5-(2'-hydroxyethylamino)-2-methylphenol, 2,4-diaminoanisole, m-toluylenediamine, resorcin, m-phenylenediamine, m-aminophenol, 4-chlororesorcin, 2-methylresorcin, 2,4-diaminophenoxyethanol, 2,6-diaminopyridine, 2-amino-3-hydroxypyridine, 4-hydroxyindole, 6-hydroxyindole, 2,4-diamino-6-hydroxypyrimidine, 2,4,6-triaminopyrimidine, 2-amino-4,6-dihydroxypyrimidine, 4-amino-2,6-dihydroxypyrimidine, 4,6-diamino-2-hydroxypyrimidine and 1,3-bis(2,4-diaminophenoxy)propane; and salts thereof.

As each of a developer and coupler, at least one of the above-exemplified ones can be used. Each of them is added in an amount of 0.01 to 20 wt. %, especially 0.5 to 10 wt. % based on the whole composition.

To the hair dye composition of the present invention, a known autoxidation dye typified by an indole or an indoline, or a known direct dye such as a nitro dye or a disperse dye can also be added.

When an anionic component (such as anionic surfactant or anionic polymer) is added to the hair dye composition of the present invention, it is preferred to satisfy the following equation:

"Ion activity concentration of the anionic component/ion activity concentration of the cationic direct dye (1)≦8"

The term "ion activity concentration" as used herein means "molar concentration x ionic valence".

Addition of a polyol, polyol alkyl ether, cationic or amphoteric polymer or silicone to the hair dye composition of the present invention is preferred, because the resulting composition can dye the hair uniformly and has improved cosmetic effects of the hair.

In addition to the above-described components, those ordinarily employed as a raw material for cosmetics can be added to the hair dye composition of the present invention. Examples of such an optional component include hydrocarbons, animal or vegetable fats and oils, higher fatty acids, organic solvents, penetration promoters, cationic surfactants, natural or synthetic polymers, higher alcohols, ethers, amphoteric surfactants, nonionic surfactants, protein derivatives, amino acids, antiseptics, chelating agents, stabilizing agents, antioxidants, plant extracts, crude drug extracts, vitamins, colorants, perfumes and ultraviolet absorbers.

The hair dye composition of the present invention can be prepared in a conventional manner into a one-part composition, a two-part composition having a first component part containing an alkali agent and a second component part containing an oxidizing agent, or a three-part composition having, in addition to these two component parts, a powdery oxidizing agent such as persulfate. The direct dye (1) can be incorporated in either one or both of these component parts of the two-part or three-part composition. When the hair dye composition of the present invention is one-part type, it is applied to the hair directly, while the two- or three-part type is applied to the hair after mixing these parts upon hair dyeing.

No particular limitation is imposed on the form of the hair dye composition of the present invention. Examples include powder, transparent liquid, emulsion, cream, gel, paste, aerosol, and aerosol foam. It preferably has a viscosity of 2000 to 100000 mPa·s in the stage of application to the hair (after mixing of all the components when the hair dye composition is a two-part or three-part type).

EXAMPLES

Examples 1 to 5

In a manner known per se in the art, hair dyes as shown in Table 1 were prepared.

TABLE 1

| | Examples (wt. %) | | | | |
|---|---|---|---|---|---|
| | 1 | 2 | 3 | 4 | 5 |
| Dye [Basic Yellow 24] | 0.2 | 0.5 | 0.15 | 0.1 | 0.2 |
| Dye [Red Dye A] | | | 0.15 | 0.1 | 0.05 |
| Dye [Basic Blue 7] | | | 0.1 | 0.1 | |
| Ethanol | | 5 | | 5 | 5 |
| Propylene glycol | | | 5 | | 5 |
| Diethylene glycol monoethyl ether | | 10 | | | |
| Guar gum | 1 | | | | |
| Hydroxypropyl guar gum | | 1 | 1 | 1 | 1 |
| "Gufquat 734" (trade name; product of ISP Japan) | 1 | | 1 | | |
| "Catinal LC100" (trade name; product of Toho Chemical Industry) | | 1 | | | 1 |
| "Polyether-modified silicone KF6005" (trade name; product of Shin-Etsu Chemical) | | | | | 0.4 |
| "Amodimethicone SM8702C" (trade name; product of Dow Corning Toray Silicone) | | | | 1.5 | |
| Monoethanolamine | | | | 0.1 | |
| Phosphoric acid | Amount to adjust pH to 9 | | | | |
| Perfume | q.s. | | | | |
| Water | Balance | | | | |

Red dye A

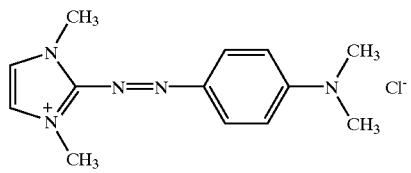

Examples 6 to 9

In a manner known per se in the art, hair dyes as shown in Table 2 were prepared.

TABLE 2

| | Examples (wt. %) | | | |
|---|---|---|---|---|
| | 6 | 7 | 8 | 9 |
| 1st part | | | | |
| Dye [Basic Yellow 24] | 0.2 | 0.1 | 0.15 | 0.2 |
| Dye [Red Dye A] | | 0.1 | | 0.05 |
| Dye [Basic Blue 99] | | 0.3 | | |
| 28 wt. % Aqueous ammonia | | | 5 | |
| Monoethanolamine | | | 2 | |
| Propylene glycol | | | 8 | |
| Polyoxyethylene (20) isostearyl ether | | | 24 | |
| Polyoxyethylene (2) isostearyl ether | | | 20 | |
| "Merquat 280" (trade name; product of Calgon Corp., a 35 wt. % aqueous solution) | 8 | | | |
| "Polymer JR400" (trade name; product of Union Carbide) | | 0.5 | | 0.5 |
| "Amodimethicone SM8702C" (trade name; product of Dow Corning Toray Silicone) | | | 2 | |
| "Polyether modified silicone KF6005" (trade name; product of Shin-Etsu Chemical) | | | | 0.3 |
| Tetrasodium ethylenediaminetetraacetate | | | 0.1 | |
| Perfume | | | q.s. | |

TABLE 2-continued

| | Examples (wt. %) | | | |
|---|---|---|---|---|
| | 6 | 7 | 8 | 9 |
| Ammonium chloride | Amount to adjust pH to 10 | | | |
| Water | Balance | | | |
| 2nd part | | | | |
| 35 wt. % Aqueous hydrogen peroxide | 17.1 | | | |
| Methylparaben | 0.1 | | | |
| Phosphoric acid | Amount to adjust pH to 3.5 | | | |
| Water | Balance | | | |

Examples 10 to 12

In a manner known per se in the art, hair dyes as shown in Table 3 were prepared.

TABLE 3

| | Examples (wt. %) | | |
|---|---|---|---|
| | 10 | 11 | 12 |
| 1st part | | | |
| Toluene-2,5-diamine | 1.9 | 1 | |
| Para-aminophenol | | | 1 |
| Resorcin | 2 | | |
| Para-amino-ortho-cresol | | | 1.1 |
| 2,4-Diaminophenoxyethanol | | 1.37 | |
| Dye [Basic Yellow 24] | 0.05 | 0.15 | 0.1 |
| 28 wt. % Aqueous ammonia | | 5 | |
| Monoethanolamine | | 2 | |
| Propylene glycol | | 8 | |
| Polyoxyethylene (20) isostearyl ether | | 24 | |
| Polyoxyethylene (2) isostearyl ether | | 20 | |
| "Merquat 280" (trade name; product of Calgon Corp., a 35 wt. % aqueous solution) | 8 | | |
| "Polymer JR400" (trade name; product of Union Carbide) | | 0.5 | |
| "Amodimethicone SM8702C" (trade name; product of Dow Corning Toray Silicone) | | | 2 |
| Sodium sulfite | | 0.05 | |
| Ascorbic acid | | 0.5 | |
| Tetrasodium ethylenediaminetetraacetate | | 0.1 | |
| Perfume | | q.s. | |
| Ammonium chloride | Amount to adjust pH to 10 | | |
| Water | Balance | | |
| 2nd part | | | |
| 35 wt. % Aqueous hydrogen peroxide | 17.1 | | |
| Methylparaben | 0.1 | | |
| Phosphoric acid | Amount to adjust pH to 3.5 | | |
| Water | Balance | | |

Example 13

In a manner known per se in the art, the following hair dye was prepared.

| | (wt. %) |
|---|---|
| (First part) | |
| Para-aminophenol | 1 |
| Para-amino-ortho-cresol | 1.1 |

-continued

| | (wt. %) |
|---|---|
| Basic Yellow 24 | 0.1 |
| 28 wt. % Aqueous ammonia | 5 |
| Monoethanolamine | 2 |
| Cetanol | 8.5 |
| Polyoxyethylene (40) cetyl ether | 3 |
| Polyoxyethylene (2) cetyl ether | 3.5 |
| Stearyl trimethyl ammonium chloride | 2 |
| Liquid paraffin | 0.5 |
| Sodium sulfite | 0.05 |
| Ascorbic acid | 0.5 |
| Tetrasodium ethylenediaminetetraacetate | 0.1 |
| Perfume | q.s. |
| Ammonium chloride | Amount to adjust pH to 10 |
| Water | Balance |
| (Second part) | |
| 35 wt. % Aqueous hydrogen peroxide | 17.1 |
| Methylparaben | 0.1 |
| Phosphoric acid | Amount to adjust pH to 3.5 |
| Water | Balance |

What is claimed is:

1. A hair dye composition comprising, as a direct dye, a compound represented by the following formula (1):

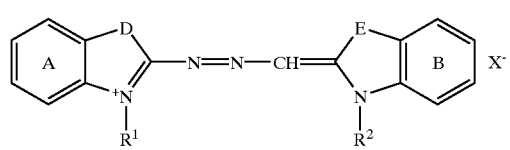

wherein, rings A and B each independently represents a benzene ring which may have a substituent and may further be cyclocondensed with another aromatic ring;

D and E each independently represents a group $NR^3$ (in which $R^3$ represents a $C_{1-6}$ alkyl group) or a sulfur atom;

$R^1$ and $R^2$ each independently represents a $C_{1-6}$ alkyl group, and $X^-$ represents an anion;

an oxidizing agent; and an oxidation dye.

2. A method comprising dyeing the hair with a hair dye composition comprising, as a direct dye, a compound represented by the following formula (1):

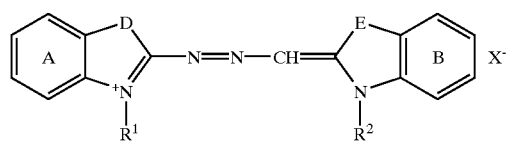

wherein, rings A and B each independently represents a benzene ring which may have a substituent and may further be cyclocondensed with another aromatic ring;

D and E each independently represents a group $NR^3$ (in which $R^3$ represents a $C_{1-6}$ alkyl group) or a sulfur atom;

$R^1$ and $R^2$ each independently represents a $C_{1-6}$ alkyl group, and $X^-$ represents an anion.

3. A hair dye composition according to claim 1, wherein the compound is Basic Yellow 24.

4. A hair dye composition according to claim 1, further comprising one or more direct dyes other than one having said formula (1).

5. A hair dye composition according to claim 1, wherein said compound of formula (1) is present in an amount of 0.01 to 20 wt. % based on the weight of the composition.

6. A hair dye composition according to claim 5, wherein said compound of formula (1) is present in an amount of 0.05 to 10 wt. % based on the weight of the composition.

7. A hair dye composition according to claim 6, wherein said compound of formula (1) is present in an amount of 0.1 to 5 wt. % based on the weight of the composition.

8. A hair dye composition according to claim 4, wherein the total amount of said direct dyes is from 0.05 to 10 wt. %, based on the weight of the composition.

9. A hair dye composition according to claim 8, wherein the total amount of dye is from 0.1 to 5 wt. %, based on the weight of the composition.

10. A hair dye composition according to claim 1, wherein the composition has a pH of 6 to 11.

11. A hair dye composition according to claim 10, wherein the composition has a pH of 8 to 11.

12. A hair dye composition according to claim 1, wherein the oxidizing agent is hydrogen peroxide.

13. A hair dye composition according to claim 1, wherein the oxidizing agent is present in an amount of 0.5 to 10 wt. % based on the weight of the composition.

14. A hair dye composition according to claim 13, wherein the oxidizing agent is present in an amount of 1 to 8 wt. % based on the weight of the composition.

15. A hair dye composition according to claim 1, wherein the oxidation dye is at least one of a color developer and a coupler, each being present in an amount of 0.01 to 20 wt. % based on the weight of the composition.

16. A hair dye composition according to claim 15, wherein the oxidation dye is at least one of a color developer and a coupler, each being present in an amount of 0.5 to 10 wt. % based on the weight of the composition.

17. A hair dye composition according to claim 1, which is a one-part composition.

18. A hair dye composition according to claim 1, which is a two-part composition having a first component part containing an alkali agent and a second component part containing the oxidizing agent.

19. A hair dye composition according to claim 1, which is a three-part composition having a first component part containing an alkali agent, a second component part containing the oxidizing agent, and a third component part containing a powdery oxidizing agent.

* * * * *